United States Patent
Löffler et al.

(10) Patent No.: US 7,297,328 B2
(45) Date of Patent: *Nov. 20, 2007

(54) SURFACTANT-FREE COSMETIC, DERMATOLOGICAL AND PHARMACEUTICAL AGENTS

(75) Inventors: Matthias Löffler, Niedernhausen (DE); Roman Morschhäuser, Mainz (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 166 days.

This patent is subject to a terminal disclaimer.

(21) Appl. No.: 10/433,175

(22) PCT Filed: Nov. 28, 2001

(86) PCT No.: PCT/EP01/13860

§ 371 (c)(1),
(2), (4) Date: Nov. 17, 2003

(87) PCT Pub. No.: WO02/44231

PCT Pub. Date: Jun. 6, 2002

(65) Prior Publication Data

US 2004/0109836 A1    Jun. 10, 2004

(30) Foreign Application Priority Data

Dec. 1, 2000 (DE) ............... 100 59 821

(51) Int. Cl.
*A61K 7/06* (2006.01)
*C08L 33/00* (2006.01)

(52) U.S. Cl. ............ 424/70.16; 424/70.1; 424/70.2; 424/70.21; 514/937; 514/772.4; 526/288; 526/277; 526/250; 526/287

(58) Field of Classification Search .......... None
See application file for complete search history.

(56) References Cited

U.S. PATENT DOCUMENTS

| | | | |
|---|---|---|---|
| 3,931,089 A | 1/1976 | Karl | 260/29.65 Q |
| 5,368,850 A | 11/1994 | Cauwet et al. | 424/70 |
| 5,879,718 A * | 3/1999 | Sebillote-Arnaud | 424/70.5 |
| 6,054,138 A | 4/2000 | Trebosc et al. | 424/401 |
| 6,120,780 A | 9/2000 | Dupuis et al. | 424/401 |
| 6,403,074 B1 | 6/2002 | Blankenburg | |
| 6,419,912 B1 | 7/2002 | Lezer | 424/78.03 |
| 6,468,549 B1 | 10/2002 | Dupuis et al. | 424/401 |
| 6,524,564 B1 * | 2/2003 | Kim et al. | 424/70.12 |

FOREIGN PATENT DOCUMENTS

| | | |
|---|---|---|
| CA | 2363079 | 8/2000 |
| EP | 0 815 828 | 1/1998 |
| EP | 0 815 844 | 1/1998 |
| EP | 0 815 845 | 1/1998 |
| FR | 2 791 558 | 10/2000 |
| WO | WO 99/04750 | 2/1999 |
| WO | WO 00/12588 | 3/2000 |

OTHER PUBLICATIONS

English abstract for JP 58-099407, "Surfactant-free emulsion cosmetics-comprising water, oil component and emulsion and consisting of water-insoluble and water absorbable polymer", Sep. 25, 1993.

* cited by examiner

*Primary Examiner*—Michael G. Hartley
*Assistant Examiner*—Jake M. Vu
(74) *Attorney, Agent, or Firm*—Richard P. Silverman

(57) ABSTRACT

The invention provides a surfactant-free cosmetic, dermatological, and pharmaceutical agents comprising at least one copolymer obtainable by free-radical copolymerization of
A) acryloyldimethyltaurine and/or acryloyldimethyltaurates,
B) optionally, one or more further olefinically unsaturated, noncationic comonomers,
C) optionally, one or more olefinically unsaturated, cationic comonomers,
D) optionally, one or more silicon-containing component(s),
E) optionally, one or more fluorine-containing component(s),
F) optionally, one or more macromonomers,
G) the copolymerization taking place if desired in the presence of at least one polymeric additive,
H) with the proviso that component A) is copolymerized with at least one component selected from one of the groups D) to G).

30 Claims, No Drawings

SURFACTANT-FREE COSMETIC, DERMATOLOGICAL AND PHARMACEUTICAL AGENTS

The present invention relates to surfactant-free cosmetic, pharmaceutical, and dermatological compositions comprising comb copolymers based on acryloyldimethyltaurine.

The cosmetic or dermatological compositions in use at the present time mostly take the form of oil-in-water emulsions (i.e., a system composed of a continuous aqueous phase and a discontinuous, dispersed oil phase) or of water-in-oil emulsions (i.e., a system composed of a continuous, fat-containing phase and a discontinuous, dispersed aqueous phase).

The water-in-oil emulsions therefore include a continuous oil phase and allow a fatty film to form at the skin surface that prevents transepidermal water loss and protects the skin against external aggressions. These emulsions are particularly suitable for protecting and enriching the skin and, in particular, for treating dry skin. The oil-in-water emulsions, for their part, impart to the skin upon application a soft, less greasy and more gentle feel than the water-in-oil emulsions.

The emulsions are generally stabilized by incorporation of emulsifying surfactants of the oil-in-water (O/W) or water-in-oil (W/O) type which by virtue of their amphiphilic structure are located at the oil/water interface and so stabilize the dispersed droplets. It is generally necessary to add these surfactants in a considerable amount—up to 10% by weight with regard to the overall weight of the emulsion—in order to obtain an appropriate stability.

These amphiphilic surfactants used in large quantity, however, may trigger an irritant effect toward the skin, eyes and/or scalp of the user. Furthermore, their use at high concentrations may lead to cosmetically unwanted effects, such as a rough, sticky and/or viscous sensation, and may give rise to a compact, heavy substance. Furthermore, the surfactants have to be selected as a function of the polarity of the oils and are therefore compatible only with a limited number of oils, thereby acryloyidimethyltaurate-based thickener systems display outstanding properties in pH ranges below pH 6.0, i.e., within a pH range in which it is no longer possible to operate with conventional poly(meth)acrylate thickeners.

A disadvantage of these acryloyldimethyltaurate-based thickener systems, however, is that stable emulsions are generally only achievable in the presence of additional surfactant coemulsifiers.

There is therefore a need for surfactant-free cosmetic, decorative, and pharmaceutical compositions which are easy to prepare, possess outstanding rheological and sensorial properties and stability, and are stable particularly in the acidic pH range.

Surprisingly it has now been found that a new class of copolymers based on acryloyidimethyltaurine (AMPS)—and suitable in the capacity of a thickener, bodying agent, emulsifier, dispersant and/or stabilizer—are outstandingly suitable for the formulation of acidic cosmetic, pharmaceutical, and dermatological compositions.

The invention accordingly provides surfactant-free cosmetic, dermatological, and pharmaceutical compositions comprising at least one copolymer obtainable by free-radical copolymerization of A) acryloyldimethyltaurine and/or acryloyldimethyltaurates,
B) if desired, one or more further olefinically unsaturated, noncationic, optionally crosslinking comonomers which have at least one oxygen, nitrogen, sulfur or phosphorus atom and possess a molecular weight of less than 500 g/mol,
C) if desired, one or more olefinically unsaturated, cationic comonomers which have at least one oxygen, nitrogen, sulfur or phosphorus atom and possess a molecular weight of less than 500 g/mol,
D) if desired, one or more silicon-containing components capable of free-radical polymerization and having a functionality of at least one,
E) if desired, one or more fluorine-containing components capable of free-radical polymerization and having a functionality of at least one,
F) if desired, one or more olefinically mono- or polyunsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E),
G) the copolymerization taking place if desired in the presence of at least one polymeric additive having number-average molecular weights of from 200 g/mol to $10^9$ g/mol,
H) with the proviso that component A) is copolymerized with at least one component selected from one of the groups D) to G).

The copolymers of the invention preferably possess a molecular weight of from $10^3$ g/mol to $10^9$ g/mol, more preferably from $10^4$ to $10^7$ g/mol, with particular preference from $5*10^4$ to $5*10^6$ g/mol.

The acryloyldimethyltaurates can be the organic or inorganic salts of acryloyldimethyltaurine (acrylamidopropyl-2-methyl-2-sulfonic acid). Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be ($C_1$-$C_{22}$)-alkyl radicals or ($C_2$-$C_{10}$)-hydroxyalkyl radicals. Preference is also given to mono- to triethoxylated ammonium compounds with different degrees of ethoxylation. It should be noted that mixtures of two or more of the abovementioned representatives are also embraced by the invention. The degree of neutralization of the acryloyldimethyltaurine can be between 0 and 100%, with particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated noncationic monomers whose reaction parameters allow copolymerization with acryloyl-dimethyltaurine and/or acryloyldimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 30.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4^+$, monoalkyl-ammonium, dialkylammonium, trialkylammonium and/or tetraalkylammonium radicals, in which the alkyl substituents of the amines independently of one another can be $(C_1-C_{22})$-alkyl radicals or $(C_2-C_{10})$-hydroxyalkyl radicals. It is additionally possible to employ mono- to triethoxylated ammonium compounds with a different degree of ethoxylation. The degree of neutralization of the carboxylic acids can be between 0 and 100%.

Further preferred comonomers B) are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethyl-acrylamide, N,N-diethylacrylamide, and N,N-diisopropylacrylamide; alkoxylated acrylamides and methacrylamides, preferably hydroxyethyl methacrylate, hydroxy-methylmethacrylamide, hydroxyethylmethacrylamide, hydroxypropylmethacryl-amide, and mono [2-(methacryloyloxy)ethyl] succinate; N,N-dimethylamino methacrylate; diethylaminomethyl methacrylate; acrylamido- and methacrylamido-glycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Suitable comonomers C) include all olefinically unsaturated monomers with cationic charge which are capable of forming copolymers with acryloyldimethyl-taurine or its salts in the chosen reaction media. The resulting distribution of the cationic charges across the chains can be random, alternating, blocklike or gradientlike. It may be noted that the cationic comonomers C) also comprehend those which bear the cationic charge in the form of a betaine, zwitterionic or amphoteric structure.

Comonomers C) for the purposes of the invention are also amino-functionalized precursors which can be converted by polymer-analogous reactions into their corresponding quaternary derivatives (e.g., reaction with dimethyl sulfate, methyl chloride), zwitterionic derivatives (e.g., reaction with hydrogen peroxide), betaine derivatives (e.g., reaction with chloroacetic acid), or amphoteric derivatives.

Particularly preferred comonomers C) are
diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride,
N-methyl-4-vinylpyridinium chloride,
dimethylaminoethyl methacrylate,
dimethylaminopropylmethacrylamide,
methacryloylethyl N-oxide and/or
methacryloylethylbetaine.

The weight fraction of the comonomers C), based on the total mass of the copolymers, can be from 0.1 to 99.8% by weight, more preferably from 0.5 to 30% by weight, and very preferably from 1 to 20% by weight.

Suitable polymerizable silicon-containing components D) are all compounds which are olefinically at least monounsaturated and capable of free-radical copolymerization under the reaction conditions chosen in each case. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicone-containing components are those of formula (I).

$$R^1-Z-[(Si(R^3R^4)-O-)_w-(Si(R^5R^6)-O_x-]-R^2 \quad (I)$$

In this formula $R^1$ represents a polymerizable function from the group of the vinylically unsaturated compounds which is suitable for the synthesis of polymeric structures by a free-radical route. $R^1$ represents preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

The attachment of the silicone-containing polymer chain to the reactive end group $R^1$ requires a suitable chemical bridge Z. Preferred bridges Z are —O—, (($C_1-C_{50}$)alkylene), —(($C_6-C_{30}$)arylene)-, —(($C_5-C_8$)cycloalkylene)-, —(($C_1-C_{50}$)alkenylene)-, -(polypropylene oxide)$_n$-, -(polyethylene oxide)$_o$-, -(polypropylene-oxide)$_n$(polyethylene oxide)$_o$-, where n and o independently of one another denote numbers from 0 to 200 and the distribution of the EO/PO units can be random or in the form of blocks. Further suitable bridge groups Z are —(($C_1-C_{10}$)alkyl)-(Si(OCH$_3$)$_2$)— and —(Si(OCH$_3$)$_2$)—.

The polymeric central moiety is represented by silicone-containing repeating units. The radicals $R^3$, $R^4$, $R^5$, and $R^6$ denote independently of one another —CH$_3$, —O—CH$_3$, —C$_6$H$_5$ or —O—C$_6$H$_5$.

The indices w and x represent stoichiometric coefficients which amount independently of one another to from 0 to 500, preferably 10 to 250. The distribution of the repeating units across the chain can be not only purely random but also blocklike, alternating or gradientlike.

$R^2$ can first be an aliphatic, olefinic, cycloaliphatic, aryaliphatic or aromatic ($C_1 - C_{50}$) hydrocarbon radical (linear or branched) or —OH, —NH$_2$, —N(CH$_3$)$_2$, —R$^7$ or stand for the structural unit [-Z-R$^1$]. The definition of the two variables Z and $R^1$ has already been explained. $R^7$ stands for further Si-containing groups. Preferred radicals $R^7$ are —O—Si(CH$_3$)$_3$, —O—Si(Ph)$_3$, —O—Si(O—Si(CH$_3$)$_3$)$_2$CH$_3$) and —O—Si(O—Si(Ph)$_3$)$_2$Ph).

If $R^2$ is an element of the group [-Z-R$^1$] the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicone-containing components are the following components with acrylic or methacrylic modification:

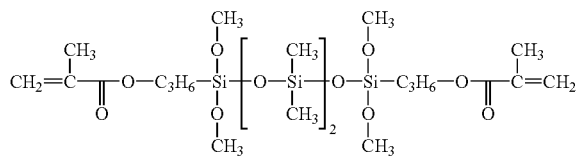

methacryloyloxypropyldimethylsilyl-endblocked polydimethylsiloxanes (f=2 to 500)

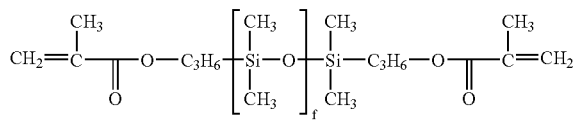

methacryloyloxypropyl-endblocked polydimethylsiloxanes (f=2 to 500)

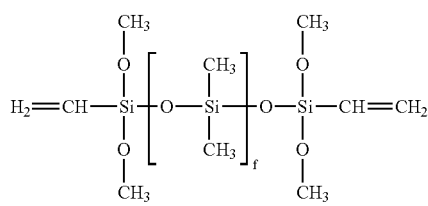

vinyldimethoxysilyl-endblocked polydimethylsiloxanes (f=2-500).

Based on the total mass of the copolymers, the amount of silicon-containing components can be up to 99.9% by weight, preferably from 0.5 to 30% by weight, more preferably from 1 to 20% by weight.

Suitable polymerizable fluorine-containing components E) include all compounds which are olefinically at least monounsaturated and which are capable of free-radical copolymerization under the reaction conditions chosen in each case. The distribution of the individual fluorine-containing monomers across the polymer chains which form need not necessarily be random. The invention also embraces the formation of blocklike (including multiblock) or gradientlike structures, for example. Combinations of two or more different fluorine-containing components E) are also possible, it being clear to the expert that monofunctional representatives lead to the formation of comb-shaped structures while di-, tri-, or polyfunctional components E) lead to structures which are at least partly crosslinked.

Preferred fluorine-containing components E) are those of formula (II).

In this formula $R^1$ represents a polymerizable function from the group of the vinylically unsaturated compounds which is suitable for the construction of polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl or methacryloyl radical.

The attachment of the fluorine-containing group to the reactive end group $R^1$ requires a suitable chemical bridge Y. Preferred bridges Y are —O—, —C(O)—, —C(O)—O—, —S—, —O—$CH_2$—CH (O—)—$CH_2$OH, —O—$CH_2$—CH (OH)—$CH_2$—O—, —O—$SO_2$—O—, —O—S(O)—O—, —PH—, —P($CH_3$)—, —$PO_3$—, —NH—, —N($CH_3$)—, —O—($C_1$-$C_{50}$)alkyl-O—, —O-phenyl-O—, —O-benzyl-O—, —O—($C_5$-$C_8$)cycloalkyl-O—, —O—($C_1$-$C_{50}$)alkenyl-O—, —O—(CH($CH_3$)—($CH_2$—O)$_n$—, —O—($CH_2$—$CH_2$—O)$_n$—, and —O—([CH—$CH_2$—O]$_n$—[$CH_2$—$CH_2$—O]$_m$)$_o$—, where n, m, and o independently of one another denote numbers from 0 to 200 and the distribution of the EO and PO units can be random or in the form of blocks. r and s are stoichiometric coefficients which independently of one another denote numbers from 0 to 200.

Preferred fluorine-containing components E) of formula (II) are
perfluorohexylethanol methacrylate,
perfluorohexoylpropanol methacrylate,
perfluoroctylethanol methacrylate,
perfluoroctylpropanol methacrylate,
perfluorohexylethanolyl polyglycol ether methacrylate,
perfluorohexoylpropanolyl poly[ethylglycol-co-propylene glycol ether] acrylate,
perfluoroctylethanolyl poly[ethylglycol-block-co-propylene glycol ether] methacrylate,
perfluoroctylpropanolyl polypropylene glycol ether methacrylate.

Based on the total mass of the copolymer the amount of fluorine-containing components can be up to 99.9% by weight, preferably from 0.5 to 30% by weight, more preferably from 1 to 20% by weight.

The macromonomers F) are at least singly olefinically functionalized polymers having one or more discrete repeating units and a number-average molecular weight of greater than or equal to 200 g/mol. In the copolymerization it is also possible to use mixtures of chemically different macromonomers F). The macromonomers are polymeric structures composed of one or more repeating units and have a molecular weight distribution characteristic of polymers.

Preferred macromonomers F) are compounds of formula (III).

$R^1$ represents a polymerizable function from the group of the vinylically unsaturated compounds which are suitable for constructing polymeric structures by a free-radical route. Preferably R' is a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

Attachment of the polymer chain to the reactive end group requires a suitable bridging group Y. Preferred bridges Y are —O—, —C(O)—, —C(O)—O—, —S—, —O—$CH_2$—CH (O—)—$CH_2$OH, —O—$CH_2$—CH(OH)—$CH_2$O—, —O—$SO_2$—O—, —O—$SO_2$—O—, —O—SO—O—, —PH—, —P($CH_3$)—, —$PO_3$—, —NH—, and —N($CH_3$)—, more preferably —O—.

The polymeric central moiety of the macromonomer is represented by the discrete repeating units A, B, C, and D. Preferably the repeating units A, B, C, and D are derived from: acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

The indices v, w, x, and z in formula (III) represent the stoichiometric coefficients relating to the repeating units A, B, C, and D. v, w, x, and z amount independently of one another to from 0 to 500, preferably 1 to 30, it being necessary for the sum of the four coefficients on average to be ≧1.

The distribution of the repeating units over the macromonomer chain can be random, blocklike, alternating or gradientlike.

$R^2$ denotes a linear or branched aliphatic, olefinic, cycloaliphatic, arylaliphatic or aromatic ($C_1$-$C_{50}$) hydrocarbon radical, OH, —$NH_2$, —$N(CH_3)_2$ or is the structural unit [—Y—$R^1$].

In the case of $R^2$ being [—Y—$R^1$] the macromonomers in question are difunctional and suitable for crosslinking the copolymers.

Particularly preferred macromonomers F) are acrylically or methacrylically monofunctionalized alkyl ethoxylates of formula (IV).

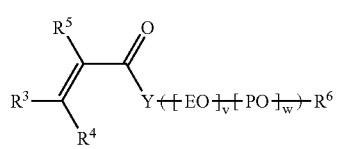

(IV)

$R^3$, $R^4$, $R^5$, and $R^6$ are independently of one another hydrogen or n-aliphatic, iso-aliphatic, olefinic, cycloaliphatic, arylaliphatic or aromatic ($C_1$-$C_{30}$) hydrocarbon radicals.

Preferably $R^3$ and $R^4$ are H or —$CH_3$, more preferably H; $R^5$ is H or —$CH_3$; and $R^6$ is an n-aliphatic, iso-aliphatic, olefinic, cycloaliphatic, arylaliphatic or aromatic ($C_1$-$C_{30}$) hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average $\geq 1$. The distribution of the EO and PO units over the macromonomer chain can be random, blocklike, alternating or gradientlike. Y stands for the abovementioned bridges.

Further particularly preferred macromonomers F) have the following structure in accordance with formula (IV):

| Name | $R^3$ | $R^4$ | $R^5$ | $R^6$ | v | w |
|---|---|---|---|---|---|---|
| ® LA-030 methacrylate | H | H | —$CH_3$ | -lauryl | 3 | 0 |
| ® LA-070 methacrylate | H | H | —$CH_3$ | -lauryl | 7 | 0 |
| ® LA-200 methacrylate | H | H | —$CH_3$ | -lauryl | 20 | 0 |
| ® LA-250 methacrylate | H | H | —$CH_3$ | -lauryl | 25 | 0 |
| ® T-080 methacrylate | H | H | —$CH_3$ | -talc | 8 | 0 |
| ® T-080 acrylate | H | H | H | -talc | 8 | 0 |
| ® T-250 methacrylate | H | H | —$CH_3$ | -talc | 25 | 0 |
| ® T-250 crotonate | —$CH_3$ | H | —$CH_3$ | -talc | 25 | 0 |
| ® OC-030 methacrylate | H | H | —$CH_3$ | -octyl | 3 | 0 |
| ® OC-105 methacrytate | H | H | —$CH_3$ | -octyl | 10 | 5 |
| ® Behenyl-010-methylaryl | H | H | H | -behenyl | 10 | 0 |
| ® Behenyl-020-methylaryl | H | H | H | -behenyl | 20 | 0 |
| ® Behenyl-010-senecionyl | —$CH_3$ | —$CH_3$ | H | -behenyl | 10 | 0 |
| ® PEG-440 diacrylate | H | H | H | -acryloyl | 10 | 0 |
| ® B-11-50 methacrylate | H | H | —$CH_3$ | -butyl | 17 | 13 |
| ® MPEG-750 methacrylate | H | H | —$CH_3$ | -methyl | 18 | 0 |
| ® P-010 acrylate | H | H | H | -phenyl | 10 | 0 |
| ® O-050-acrylate | H | H | H | -oleyl | 5 | 0 |

Further particularly suitable macromonomers F) are esters of (meth)acrylic acid with ($C_{10}$-$C_{18}$) fatty alcohol polyglycol ethers having 8 EO units (Genapol® C-080)

$C_{11}$ oxo alcohol polyglycol ethers having 8 EO units (Genapol® UD-080)

($C_{12}$-$C_{14}$) fatty alcohol polyglycol ethers having 7 EO units (Genapol® LA-070)

($C_{12}$-$C_{14}$) fatty alcohol polyglycol ethers having 11 EO units (Genapol® LA-110)

($C_{16}$-$C_{18}$) fatty alcohol polyglycol ethers having 8 EO units (Genapol® T-080)

($C_{16}$-$C_{18}$) fatty alcohol polyglycol ethers having 15 EO units (Genapol® T-150)

($C_{16}$-$C_{18}$) fatty alcohol polyglycol ethers having 11 EO units (Genapol® T-110)

($C_{16}$-$C_{18}$) fatty alcohol polyglycol ethers having 20 EO units (Genapol® T-200)

($C_{16}$-$C_{18}$) fatty alcohol polyglycol ethers having 25 EO units (Genapol® T-250)

($C_{18}$-$C_{22}$) fatty alcohol polyglycol ethers having 25 EO units and/or iso-($C_{16}$-$C_{18}$) fatty alcohol polyglycol ethers having 25 EO units.

The Genapol® grades are products of Clariant GmbH.

The molecular weight of the macromonomers F) is preferably from 200 g/mol to $10^6$ g/mol, more preferably from 150 to $10^4$ g/mol, and very preferably from 200 to 5 000 g/mol.

Based on the total mass of the copolymers it is possible for the amount of macromonomers to be up to 99.9% by weight. Preferred ranges used are from 0.5 to 30% by weight and from 70 to 99.5% by weight. Particularly preferred are ranges from 1 to 20% by weight and from 75 to 95% by weight.

Preferred copolymers are those obtainable by copolymerizing at least components A), C) and D).

Further preferred copolymers are those obtainable by copolymerizing at least components A), C) and E).

Further preferred copolymers are those obtainable by copolymerizing at least components A), C) and F).

Further preferred copolymers are those obtainable by copolymerizing at least components A), D) and F).

Further preferred copolymers are those obtainable by copolymerizing at least components A) and F).

Further preferred copolymers are those obtainable by copolymerizing at least components A) and D).

Further preferred copolymers are those obtainable by copolymerizing at least components A) and E).

In one preferred embodiment the copolymerization is conducted in the presence of at least one polymeric additive G), the additive G) being added wholly or partly in solution to the polymerization medium before the actual copolymerization. The use of two or more additives G) is likewise in accordance with the invention.

Crosslinked additives G) may likewise be used.

The additives G) or mixtures thereof must only be wholly or partly soluble in the chosen polymerization medium. During the actual polymerization step the additive G) has a number of functions. On the one hand it prevents the formation of overcrosslinked polymer fractions in the copolymer which forms in the actual polymerization step, and on the other hand the additive G) is statistically attacked by active free radicals in accordance with the very well-known mechanism of graft copolymerization. Depending on the particular additive G), this results in greater or lesser fractions of the additive being incorporated into the copolymers. Moreover, suitable additives G) possess the property of altering the solution parameters of the copolymers which form during the free-radical polymerization reaction in such a way that the average molecular weights are shifted to higher values. As compared with analogous copolymers prepared without the addition of the additives G), those prepared with the addition of additives G) advantageously exhibit a significantly higher viscosity in aqueous solution.

Preferred additives G) are homopolymers and copolymers which are soluble in water and/or alcohols, preferably in t-butanol. The term "copolymers" also comprehends those having more than two different monomer types.

Particularly preferred additives G) are homopolymers and copolymers of N-vinyl-formamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyidimethylammonium chloride (DADMAC) and/or [2-(methacryloyloxy)ethyl]-trimethylammonium chloride (MAPTAC); polyalkylene glycols and/or alkylpolyglycols.

Particularly preferred additives G) are polyvinylpyrrolidones (e.g., Luviskol K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives G) is preferably from $10^2$ to $10^7$ g/mol, more preferably from $0.5*10^4$ to $10^6$ g/mol.

The amount in which the polymeric additive G) is used, based on the total mass of the monomers to be polymerized during the copolymerization, is preferably from 0.1 to 90% by weight, more preferably from 1 to 20% by weight, and with particular preference from 1.5 to 10% by weight.

In another preferred embodiment the copolymers of the invention are crosslinked, i.e., they contain comonomers having at least two polymerizable vinyl groups.

Preferred crosslinkers are methylenebisacrylamide; methylenebismethacrylamide; esters of unsaturated monocarboxylic and polycarboxylic acids with polyols, preferably diacrylates and triacrylates, dimethacrylates and trimethacrylates, more preferably butanediol and ethylene glycol diacrylate and methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylene-diamine; allyl esters of phosphoric acid; and/or vinylphosphonic acid derivatives. A particularly preferred crosslinker is trimethylolpropane triacrylate (TMPTA). The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electro-magnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example. Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(ll) sulfate, etc.) or redox systems comprising as reducing component an aliphatic or aromatic sulfonic acid (e.g., benzenesulfonic acid, toluenesulfonic acid, etc.).

Serving as the polymerization medium may be any solvents which are very substantially inert in respect of free-radical polymerization reactions and which allow the development of high molecular weights. Use is preferably made of water and lower, tertiary alcohols or hydrocarbons having 3 to 30 carbon atoms. In one particularly preferred embodiment t-butanol is used as the reaction medium. Mixtures of two or more representatives of the potential solvents described are of course likewise in accordance with the invention. This also includes emulsions of mutually immiscible solvents (e.g., water/hydrocarbons). In principle, all kinds of reaction regime leading to the polymer structures of the invention are suitable (solution polymerization, emulsion methods, precipitation methods, high-pressure methods, suspension methods, bulk polymerization, gel polymerization, and so on). Preferred suitability is possessed by precipitation polymerization, particularly preferred suitability by precipitation polymerization in tert-butanol.

The following list shows 67 copolymers suitable with particular advantage for formulating the compositions of the invention. The different copolymers 1 to 67 are obtainable in accordance with the following preparation processes 1, 2, 3, and 4.

Process 1:

These polymers can be prepared by the precipitation method in tert-butanol. The monomers were introduced in t-butanol, the reaction mixture was rendered inert, and then, after initial heating to 60° C., the reaction was initiated by addition of the corresponding t-butanol-soluble initiator (preferably dilauroyl peroxide). After the end of reaction (2 hours) the polymers were isolated by removal of the solvent under suction and by subsequent vacuum drying.

Process 2:

These polymers are preparable by the gel polymerization method in water. The monomers are dissolved in water, the reaction mixture is rendered inert, and then, after initial heating to 65° C., the reaction is initiated by addition of suitable initiators or initiator systems (preferably $Na_2S_2O_8$). The polymer gels are subsequently comminuted and the polymers are isolated after drying.

Process 3:

These polymers are preparable by the emulsion method in water. The monomers are emulsified in a mixture of water/organ. solvent (preferably cyclohexane) using an emulsifier, the reaction mixture is rendered inert by means of $N_2$, and then, after initial heating to 80° C., the reaction is initiated by addition of suitable initiators or initiator systems (preferably $Na_2S_2O_8$). The polymer emulsions are subsequently evaporated down (with cyclohexane acting as an azeotrope former for water) and the polymers are thereby isolated.

Process 4:

These polymers are preparable by the solution method in organic solvents (preferably toluene, also, for example, tertiary alcohols). The monomers are introduced in the solvent, the reaction mixture is rendered inert, and then, after initial heating to 70° C., the reaction is initiated by addition of suitable initiators or initiator systems (preferably dilauroyl peroxide). The polymers are isolated by evaporating off the solvent and by subsequent vacuum drying.

Polymers having hydrophobic side chains, uncrosslinked

| No. | Composition | Preparation process |
|---|---|---|
| 1 | 95 g AMPS 5 g Genapol T-080 | 1 |
| 2 | 90 g AMPS 10 g Genapol T-080 | 1 |
| 3 | 85 g AMPS 15 g Genapol T-080 | 1 |
| 4 | 80 g AMPS 20 g Genapol T-080 | 1 |
| 5 | 70 g AMPS 30 g Genapol T-080 | 1 |
| 6 | 50 g AMPS 50 g Genapol T-080 | 3 |
| 7 | 40 g AMPS 60 g Genapol T-080 | 3 |
| 8 | 30 g AMPS 70 g Genapol T-080 | 3 |
| 9 | 20 g AMPS 80 g Genapol T-080 | 3 |
| 10 | 60 g AMPS 60 g BB10 | 4 |
| 11 | 80 g AMPS 20 g BB10 | 4 |
| 12 | 90 g AMPS 10 g BB10 | 3 |
| 13 | 80 g AMPS 20 g BB10 | 1 |
| 14 | 80 g AMPS 20 g Genapol LA040 | 1 |

Polymers having hydrophobic side chains, crosslinked

| No. | Composition | Preparation process |
|---|---|---|
| 15 | 80 g AMPS 20 g Genapol LA040 0.6 g AMA | 1 |
| 16 | 80 g AMPS 20 g Genapol LA040 0.8 g AMA | 1 |
| 17 | 80 g AMPS 20 g Genapol LA040 1.0 g AMA | 1 |
| 18 | 628.73 g AMPS 120.45 g Genapol T-250 6.5 g TMPTA | 2 |
| 19 | 60 g AMPS 40 g BB10 1.9 g TMPTA | 4 |
| 20 | 80 g AMPS 20 g BB10 1.4 g TMPTA | 4 |
| 21 | 90 g AMPS 10 g BB10 1.9 g TMPTA | 4 |
| 22 | 80 g AMPS 20 g BB10 1.9 g TMPTA | 4 |
| 23 | 60 g AMPS 40 g BB10 1.4 g TMPTA | 4 |

Polymers having hydrophobic side chains, crosslinked, grafted

| No. | Composition | Preparation process |
|---|---|---|
| 24 | 95 g AMPS 5 g BB10, 1.9 g TMPTA, 1 g Poly-NVP | 1 |
| 25 | 90 g AMPS 10 g BB10, 1.9 g TMPTA, 1 g Poly-NVP | 1 |
| 26 | 85 g AMPS 15 g BB10, 1.9 g TMPTA, 1 g Poly-NVP | 1 |
| 27 | 90 g AMPS 10 g BB10, 1.9 g TMPTA, 1 g Poly-NVP | 1 |

Polymers having silicon-containing groups, uncrosslinked

| No. | Composition | Preparation process |
|---|---|---|
| 28 | 80 g AMPS, 20 g Silvet 867 | 1 |
| 29 | 80 g AMPS, 50 g Silvet 867 | 4 |

Polymers having silicon-containing groups, crosslinked

| No. | Composition | Preparation process |
|---|---|---|
| 30 | 80 g AMPS, 20 g Silvet 867, 0.5 g MBA | 4 |
| 31 | 80 g AMPS, 20 g Silvet 867, 1.0 g MBA | 1 |
| 32 | 60 g AMPS, 40 g Y-12867, 0.95 g AMA | 1 |
| 33 | 80 g AMPS, 20 g Y-12867, 0.95 g AMA | 1 |
| 34 | 90 g AMPS, 10 g Y-12867, 0.95 g AMA | 1 |
| 35 | 60 g AMPS, 40 g Silvet 7280, 0.95 g AMA | 1 |
| 36 | 80 g AMPS, 20 g Silvet 7280, 0.95 g AMA | 1 |
| 37 | 90 g AMPS, 10 g Silvet 7280, 0.95 g AMA | 1 |
| 38 | 60 g AMPS, 40 g Silvet 7608, 0.95 g AMA | 1 |
| 39 | 80 g AMPS, 20 g Silvet 7608, 0.95 g AMA | 1 |
| 40 | 90 g AMPS, 10 g Silvet 7608, 0.95 g AMA | 1 |

Polymers having hydrophobic side chains and cationic groups, uncrosslinked

| No. | Composition | Preparation process |
|---|---|---|
| 41 | 87.5 g AMPS, 7.5 g Genapol T-110, 5 g DADMAC | 2 |
| 42 | 40 g AMPS, 10 g Genapol T110, 45 g methacrylamide | 2 |
| 43 | 55 g AMPS, 40 g Genapol LA040, 5 g Quat | 1 |
| 44 | 75 g AMPS, 10 g BB10, 6.7 g Quat | 1 |

Polymers having hydrophobic side chains and cationic groups, crosslinked

| No. | Composition | Preparation process |
|---|---|---|
| 45 | 60 g AMPS, 20 g Genapol T-80, 10 g Quat, 10 g HEMA | 1 |
| 46 | 75 g AMPS, 20 g Genapol T-250, 5 g Quat, 1.4 g TMPTA | 1 |
| 47 | 75 g AMPS, 20 g Genapol T-250, 10 g Quat, 1.4 g TMPTA | 1 |
| 48 | 75 g AMPS, 20 g Genapol T-250, 20 g Quat, 1.4 g TMPTA | 1 |

Polymers having fluorine-containing groups

| No. | Composition | Preparation process |
|---|---|---|
| 49 | 94 g AMPS, 2.02 g Fluowet AC 600 | 1 |
| 50 | 80 g AMPS, 20 g perfluorooctylpolyethylene glycol methacrylate, 1 g Span 80 | 3 |

Polymers having fluorine-containing groups, grafted

| No. | Composition | Preparation process |
|---|---|---|
| 51 | 80 g AMPS, 10 g Fluowet AC 600, 5 g Poly-NVP | 1 |
| 52 | 70 g AMPS, 8 g perfluorooctylethyloxyglyceryl methacrylate, 5 g Poly-NVP | 4 |

Polyfunctional polymers

| No. | Composition | Preparation process |
|---|---|---|
| 53 | 80 g AMPS, 10 g Genapol LA070, 10g Silvet 7608, 1.8 g TMPTA | 1 |
| 54 | 70 g AMPS, 5 g N-vinylpyrrolidone, 15 g Genapol T-250 methacrylate, 10 g Quat, 10 g Poly-NVP | 4 |
| 55 | 80 g AMPS, 5 g N-vinylformamide, 5 g Genapol O-150 methacrylate, 10 g DADMAC, 1.8 g TMPTA, 8 g poly-N-vinylformamide | 2 |
| 56 | 70 g AMPS, 5 g N-vinylpyrrolidone, 15 g Genapol T-250 methacrylate, 10 g Quat, 10 g Poly-NVP | 1 |
| 57 | 60 g AMPS, 10 g Genapol-BE-020 methacrylate, 10 g Genapol T-250 acrylate, 20 g Quat, 1 g Span 80 | 1 |
| 58 | 60 g AMPS, 20 g MPEG-750 methacrylate, 10 g methacryloyloxypropyldimethicone, 10 g perfluorooctylpolyethylene glycol methacrylate, 10 g poly[N-vinylcaprolactone-co-acrylic acid] (10/90) | 1 |
| 59 | 80 g AMPS, 5 g N-vinylformamide, 5 g Genapol O-150 methacrylate, 10 g DADMAC, 1.8 g TMPTA | 1 |
| 60 | 70 g AMPS, 10 g Genapol T-250 acrylate, 5 g N-methyl-4-vinylpyridinium chloride, 2.5 g Silvet Y-12867, 2.5 g perfluorohexylpolyethylene glycol methacrylate, 10 g polyethylene glycol dimethacrylate, 4 g poly[N-vinylcaprolactam] | 1 |
| 61 | 10 g AMPS, 20 g acrylamide, 30 g N-2-vinylpyrrolidone, 20 g Silvet 7608, 10 g methacryloyloxypropyldimethicone, 10 g Fluowet AC 812 | 3 |
| 62 | 60 g AMPS, 10 g DADMAC, 10 g Quat, 10 g Genapol-LA-250 crotonate, 10 g methacryloyloxypropyldimethicone, 7 g poly[acrylic acid-co-N-vinylformamide] | 1 |
| 63 | 50 g AMPS, 45 g Silvet 7608, 1.8 g TMPTA, 8 g poly[N-vinylformamide] | 1 |
| 64 | 20 g AMPS, 10 g Genapol T 110, 35 g MAA, 30 g HEMA, 5 g DADMAC | 4 |
| 65 | 20 g AMPS, 80 g BB10, 1.4 g TMPTA | 1 |
| 66 | 75 g AMPS, 20 g BB10, 6.7 g Quat, 1.4 g TMPTA | 1 |
| 67 | 35 g AMPS, 60 g acrylamide, 2 g VIFA, 2.5 g vinylphosphonic acid, 2 mol % Fluowet EA-600 | 4 |

Chemical designation of the reactants:

| | |
|---|---|
| AMPS | acryloyldimethyltaurate, preferably Na or NH4 salt |
| Genapol ® T-080 | $C_{16}$-$C_{18}$ fatty alcohol polyglycol ether having 8 EO units |
| Genapol ® T-110 | $C_{12}$-$C_{14}$ fatty alcohol polyglycol ether having 11 EO units |
| Genapol ® T-250 | $C_{16}$-$C_{18}$ fatty alcohol polyglycol ether having 25 EO units |
| Genapol ® LA-040 | $C_{12}$-$C_{14}$ fatty alcohol polyglycol ether having 4 EO units |
| Genapol ® LA-070 | $C_{12}$-$C_{14}$ fatty alcohol polyglycol ether having 7 EO units |
| Genapol ® O-150 methacrylate | $C_{16}$-$C_{18}$ fatty alcohol polyglycol ether methacrylate having 15 EO units, |
| Genapol ® LA-250 crotonate | $C_{12}$-$C_{14}$ fatty alcohol polyglycol ether crotonate having 25 EO units |
| Genapol ® T-250 methacrylate | $C_{16}$-$C_{18}$ fatty alcohol polyglycol ether methacrylate having 25 EO units |
| Genapol ® T-250 acrylate | $C_{16}$-$C_{18}$ fatty alcohol polyglycol ether acrylate having 25 EO units |
| BB10 ® | polyoxyethylene(10)behenyl ether |
| TMPTA | trimethylolpropane triacrylate |
| Poly-NVP | poly-N-vinylpyrrolidone |
| Silvet ® 867 | siloxane-polyalkylene oxide copolymer |
| MBA | methylenebisacrylamide |
| AMA | allyl methacrylate |
| ®Y-12867 | siloxane-polyalkylene oxide copolymer |
| Silvet ® 7608 | polyalkylene oxide-modified heptamethyltrisiloxane |
| Silvet ® 7280 | polyalkylene oxide-modified heptamethyltrisiloxane |
| DADMAC | diallyldimethylammonium chloride |
| HEMA | 2-hydroxyethyl methacrylate |
| Quat | 2-(methacryloyloxy)ethyltrimethylammonium chloride |
| Fluowet ® AC 600 | perfluoroalkylethyl acrylate |
| Span ® 80 | sorbitan ester |

In one preferred embodiment the copolymers are water-soluble or water-swellable. The acryloyidimethyltaurate comb copolymers described display advantageous properties in both crosslinked and noncrosslinked form.

The described grafting of the acryloyidimethyltaurate comb copolymers with other polymers, which can be carried out optionally, leads to products having a particular polymer morphology and giving rise to optically clear gels in aqueous systems. A potential disadvantage of the copolymers without grafting is a more or less strong opalescence in aqueous solution. The basis for this opalescence is hitherto unavoidable, overcrosslinked polymer fractions which arise in the course of the synthesis and are inadequately swollen in water. This produces light-scattering particles whose size is well above the wavelength of visible light and which are therefore the cause of the opalescence. The described grafting process, which can be carried out optionally, substantially reduces or entirely prevents the formation of over-crosslinked polymer fractions in relation to conventional techniques.

The described incorporation both of cationic charges and of silicon, fluorine or phosphorus atoms into the acryloyidimethyltaurate comb copolymers, which can be carried out optionally, leads to products which in cosmetic formulations possess particular sensorial and rheological properties. An improvement in the sensorial and rheological properties may be desired in particular in the context of use in rinse-off products (especially hair treatment compositions) or leave-on products (especially O/W emulsions).

Based on the finished compositions, the compositions of the invention contain preferably from 0.01 to 10% by weight, more preferably from 0.1 to 5% by weight, very preferably from 0.5 to 3% by weight, of copolymers.

The compositions of the invention may further comprise one or more acidic organic active substances. Preferred compounds are those selected from glycolic acid, lactic acid, citric acid, tartaric acid, mandelic acid, salicylic acid, ascorbic acid, pyruvic acid, oligooxa-monocarboxylic and -dicarboxylic acids, alpha-hydroxy acids, fumaric acid, retinoic acid, sulfonic acids, benzoic acid, kojic acid, fruit acid, malic acid, gluconic acid, and derivatives thereof.

The formulations are normally adjusted to a pH in the range from 2 to 12, preferably from 3 to 8.

The compositions can be on an aqueous or aqueous-alcoholic base, and examples include hair gels.

The compositions may further comprise emulsions and suspensions which comprise copolymers as thickeners, dispersants, emulsifiers, suspension media with a thickening effect, and bodying agents.

They may also be decorative preparations which contain solids and which comprise the copolymers as lubricants, adhesives, thickeners, dispersants, and emulsifiers.

The emulsifying, stabilizing and/or bodying effect of the copolymers in emulsions is due to and/or boosted by association of the polymer side chains with one another and also the interaction of the polymer side chains with the hydrophobic oil components.

Besides a cosmetically and/or dermatologically acceptable aqueous medium, the formulations may comprise organic solvents. These solvents are preferably selected from the group consisting of monohydric and polyhydric alcohols, optionally ethoxylated polyethylene glycols, propylene glycol esters, sorbitol and its derivatives, glycol ethers, propylene glycol ethers, and fatty esters, and are used, based on the finished compositions, at up to 90% by weight, preferably from 5 to 70% by weight.

The oil fraction of the emulsions is normally up to 95% by weight, preferably from 2 to 50% by weight, more preferably from 5 to 20% by weight. The fraction of oily substances is dependent inter alia on whether lotions, with a comparatively low viscosity, or creams and ointments, of high viscosity, are to be prepared. The emulsions can be either water-in-oil emulsions or oil-in-water emulsions.

The emulsions can be used as skincare compositions, such as day creams, night creams, beauty creams, nutrient cream, body lotions, ointments and the like, for example, and as further auxiliaries and additives may comprise cationic polymers, film formers, and also other additions customary in cosmetology, such as superfatting agents, moisturizing agents, stabilizers, active biogenic substances, glycerol, preservatives, pearlizing agents, dyes and fragrances, solvents, hydrotropic agents, opacifiers, further thickeners and dispersants, and also protein derivatives such as gelatin, collagen hydrolysates, natural or synthetic-based polypeptides, egg yolk, lecithin, lanolin and lanolin derivatives, deodorants, substances with a keratolytic and keratoplastic action, enzymes and carrier substances, antioxidants, UV light protection filters, pigments and metal oxides, and antimicrobial agents.

An oily substance is any fatty substance which is liquid at room temperature (25° C.).

The fatty phase may therefore comprise one or more oils selected preferably from the following oils:

silicone oils, volatile or nonvolatile, linear, branched or cyclic, optionally with organic modification; phenylsilicones; silicone resins and silicone gums; mineral oils such as paraffin oil or vaseline oil; oils of animal origin such as perhydrosqualene, lanolin; oils of plant origin such as liquid triglycerides, e.g., sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, and coconut oil;

synthetic oils such as purcellin oil, isoparaffins, linear and/or branched fatty alcohols and fatty acid esters, preferably guerbet alcohols having 6 to 18, preferably 8 to 10, carbon atoms; esters of linear ($C_6$-$C_{13}$) fatty acids with linear ($C_6$-$C_{20}$) fatty alcohols; esters of branched ($C_6$-$C_{13}$) carboxylic acids with linear ($C_6$-$C_{20}$) fatty alcohols, esters of linear ($C_6$-$C_{18}$) fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on ($C_6$-$C_{10}$) fatty acids;

esters such as dioctyl adipate, diisopropyl dimer dilinoleate; propylene glycols/dicaprylate or waxes such as beeswax, paraffin wax or microwaxes, alone or in combination with hydrophilic waxes, such as cetylstearyl alcohol, for example; fluorinated and perfluorinated oils; fluorinated silicone oils; mixtures of the aforementioned compounds.

Suitable nonionogenic coemulsifiers include adducts of from 0 to 30 mol of ethylene oxide and/or from 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; ($C_{12}$-$C_{18}$) fatty acid monoesters and diesters of adducts of from 0 to 30 mol of ethylene oxide with glycerol; glycerol monoesters and diesters and sorbitan monoesters and diesters of saturated and unsaturated fatty acids having 6 to 22 carbon atoms and, where appropriate, their ethylene oxide adducts; adducts of from 15 to 60 mol of ethylene oxide with castor oil and/or hydrogenated castor oil; polyol esters and especially polyglycerol esters, such as polyglyceryl polyricinoleate and polyglyceryl poly-12-hydroxystearate, for example. Likewise suitable are mixtures of compounds from one or more of these classes of substance.

Suitable cationic polymers include those known under the INCI designation "Polyquaternium", especially Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and also Polyquaternium 37&mineral oil&PPG trideceth (Salcare SC95), PVP-dimethylaminoethyl methacrylate copolymer, guar-hydroxypropyltriammonium chlorides, and also calcium alginate and ammonium alginate. It is additionally possible to employ cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyldiethylenetriamine; polyaminopolyamide and cationic chitin derivatives, such as chitosan, for example.

Examples of suitable silicone compounds are dimethylpolysiloxane, methylphenylpolysiloxanes, cyclic silicones, and amino-, fatty acid-, alcohol-, polyether-, epoxy-, fluoro- and/or alkyl-modified silicone compounds, and also polyalkylsiloxanes, polyalkylarylsiloxanes, polyethersiloxanes, as described in U.S. Pat. No. 5,104,645 and the documents cited therein, which at room temperature may be present either in liquid form or in resin form.

Suitable film formers, depending on the intended application, include water-soluble polyurethanes, for example, $C_{10}$-polycarbamyl polyglyceryl esters, polyvinyl alcohol, polyvinylpyrrolidone, copolymers thereof, for example vinylpyrrolidone/vinyl acetate copolymers, water-soluble acrylic acid copolymers and their esters or salts, examples being partial ester copolymers of acrylic/methacrylic acid and polyethylene glycol ethers of fatty alcohols, such as acrylate/steareth-20 methacrylate copolymers, water-soluble cellulose, examples being hydroxymethylcellulose, hydroxyethylcellulose, hydroxypropylcellulose, water-soluble quaterniums, polyquaterniums, carboxyvinyl polymers, such as carbomers and their salts, polysaccharides, polydextrose for example, and glucan.

As superfatting agents it is possible to use substances such as, for example, polyethoxylated lanolin derivatives, lecithin derivatives, polyol fatty acid esters, monoglycerides, and fatty acid alkanol amides, the latter serving simultaneously as foam stabilizers. Moisturizers available include for example isopropyl palmitate, glycerol and/or sorbitol.

As stabilizers it is possible to use metal salts of fatty acids, such as magnesium, aluminum and/or zinc stearate, for example.

Active biogenic substances are to be understood as including, for example, plant extracts and vitamin complexes.

The compositions of the invention can be blended with conventional ceramides, pseudoceramides, fatty acid N-alkylpolyhydroxyalkyl amides, cholesterol, cholesterol fatty acid esters, fatty acids, triglycerides, cerebrosides, phospholipids, and similar substances as a care additive.

Suitable UV filters include for example 4-aminobenzoic acid; 3-(4'-trimethyl-ammonium)benzylideneboran-2-one methylsulfate; 3,3,5-trimethylcyclohexyl salicylate; 2-hydroxy-4-methoxybenzophenone; 2-phenylbenzimidazole-5-sulfonic acid and its potassium, sodium, and triethanolamine salts; 3,3'-(1,4-phenylene-dimethine)bis(7,7-dimethyl-2-oxobicyclo[2.2.1]heptane-1-methanesulfonic acid and its salts; 1-(4-tert-butylphenyl)-3-(4-methoxyphenyl)propane-1,3-dione;

3-(4'-sulfo)benzylidenebornan-2-one and its salts; 2-ethylhexyl 2-cyano-3,3-diphenylacrylate; polymer of N-[2(and 4)-(2-oxoborn-3-ylidenemethyl)benzyl]-acrylamide; 2-ethylhexyl 4-methoxycinnamate; ethoxylated ethyl 4-aminobenzoate; isoamyl 4-methoxycinnamate; 2,4,6-tris[p-(2-ethylhexyloxycarbonyl)anilino]-1,3,5-triazine;
2-(2H-benzotriazol-2-yl)-4-methyl-6-(2-methyl-3-(1,3,3,3-tetramethyl-1-(trimethylsilyloxy)disiloxanyl)propyl)phenol;
4,4'-[(6-[4-((1,1-dimethylethyl)aminocarbonyl)phenylamino]-1,3,5-triazin-2,4-yl)diimino]bis(benzoic acid 2-ethylhexyl ester);
3-(4'-methylbenzylidene)-D,L-camphor; 3-benzylidenecamphor; 2-ethylhexyl salicylate; 2-ethylhexyl 4-dimethylaminobenzoate; hydroxy-4-methoxybenzo-phenone-5-sulfonic acid (sulisobenzone) and the sodium salt; and/or 4-isopropyl-benzyl salicylate.

As pigments/micropigments it is possible for example to use microfine titanium dioxide, mica-titanium oxide, iron oxides, mica-iron oxide, zinc oxide, silicon oxides, ultramarine blue, and chromium oxides.

Examples of suitable antioxidants include superoxide dismutase, tocopherol (vitamin E), and ascorbic acid (vitamin C).

Examples of suitable preservatives include phenoxyethanol, parabens, pentanediol or sorbic acid.

As dyes it is possible to use the substances which are suitable and approved for cosmetic purposes.

Suitable active antifungal substances (fungicides) include preferably ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, Zn pyrithione, and octopirox.

Essential to the invention is that the described acryloyldimethyltaurate copolymers can be used even in the absence of an additional nonsurfactant coemulsifier (e.g., polymeric emulsifiers) and/or in the absence of an additional bodying agent. The presence of nonsurfactant coemulsifiers and/or bodying agents is therefore not mandatory, though is possible. Combination with other known nonsurfactant coemulsifiers and/or bodying agents may be desirable in order to set specific cosmetic profiles and to exploit synergistic effects.

The qualities achieved are extremely innovative: the emulsions are creamy and ointmentlike and above all do not have the gellike or even gelatinelike appearance of certain prior art emulsions in which the external aqueous phase is thickened. The cosmetic feel on the skin is also very good. Upon application the emulsion imparts a sensation of freshness and of comfort, and at the same time has a rich and nourishing effect; it is soft and luxurious and in no way sticky. Emulsions of the invention can be prepared in a conventional manner, by hot, hot-hot/cold, or PIT emulsification, for example.

The examples which follow are intended to illustrate the invention, though without restricting it thereto (the percentages are by weight). The copolymers used in the examples are representatives of the particularly preferred copolymers 1 to 67 already listed in the description. They were prepared by the therein-indicated processes 1, 2, 3 or 4 using the preferred initiators and solvents.

EXAMPLE 1

O/W Skin Milk with Keratolytic Effect, Surfactant-free Composition

| | | |
|---|---|---|
| A | Copolymer No. 15 | 1.0% |
| | Mineral oil | 4.00% |
| | Almond oil | 4.00% |
| | ®Cetiol SN (Henkel) | 8.00% |
| | Cetearyl isononanoate | |
| B | ®Aristoflex AVC (Clariant) | 0.30% |
| | Ammonium acryloyldimethyltaurate/ VP copolymer | |
| C | Water | ad 100% |
| | Citric acid | 0.30% |
| | Malic acid | 0.40% |
| | Glycolic acid | 0.70% |
| | Lactic acid | 0.70% |
| D | Fragrances | 0.30% |

Preparation

| I | Mix A and B. |
|---|---|
| II | Mix the components C. |
| III | Add II to I. |
| II | Stir D into I. |
| III | Homogenize emulsion, pH 3.5. |

EXAMPLE 2

Surfactant-free Moisturizing Lotion

| A | Almond oil | 7.00% |
|---|---|---|
|   | Cyclomethicone | 5.00% |
| B | Copolymer No. 18 | 1.50% |
| C | Glycerol | 7.00% |
|   | Water | ad 100% |
|   | Preservative | q.s. |
| D | Fragrance | 0.30% |

Preparation

| I | Mix A and B. |
|---|---|
| II | Stir solution of C into I. |
| III | Add D to II. |
| IV | Homogenize. |
| V | pH 5.5. |

EXAMPLE 3

Refreshing, Surfactant-free Lotion

| A | Almond oil | 7.00% |
|---|---|---|
|   | Cyclomethicone | 5.00% |
| B | Copolymer No. 32 | 1.50% |
| C | Glycerol | 3.00% |
|   | Ethanol | 20.00% |
|   | Water | ad 100% |
|   | Preservative | q.s. |
| D | Fragrance | 0.30% |

Preparation

| I | Mix A and B. |
|---|---|
| II | Stir solution of C into I. |
| III | Add D to II. |
| IV | Homogenize. |

EXAMPLE 4

Surfactant-free Lotion with Refreshing, Vivifying Effect

| A | Jojoba oil | 5.00% |
|---|---|---|
|   | Almond oil | 3.00% |
|   | Cetiol V | 3.00% |
|   | Decyl oleate | |

| B | Copolymer No. 35 | 1.50% |
|---|---|---|
| C | Glycerol | 3.00% |
|   | Menthol | 0.70% |
|   | Camphor | 0.30% |
|   | Ethanol | 5.00% |
|   | Water | ad 100% |
|   | Preservative | q.s. |
| D | Fragrance | 0.30% |

Preparation

| I | Mix A and B. |
|---|---|
| II | Stir solution of C into I. |
| III | Add D to II. |
| IV | Homogenize. |
| V | Adjust pH to 6.00. |

What is claimed is:

1. A surfactant-free cosmetic, dermatological or pharmaceutical composition which is free of surfactant and comprises at least one copolymer obtained by free-radical copolymerization of
   A) acryloyldimethyltaurine and/or acryloyldimethyltaurates,
   B) optionally, one or more further olefinically unsaturated, noncationic comonomer which has at least one oxygen, nitrogen, sulfur or phosphorus atom and possess a molecular weight of less than 500 g/mol,
   C) optionally, one or more olefinically unsaturated, cationic comonomer which has at least one oxygen, nitrogen, sulfur or phosphorus atom and possess a molecular weight of less than 500 g/mol,
   D) one or more silicon-containing component a) capable of free-radical polymerization and having a functionality of at least one, where at least one silicon-containing component a) is a compound selected from the formulae

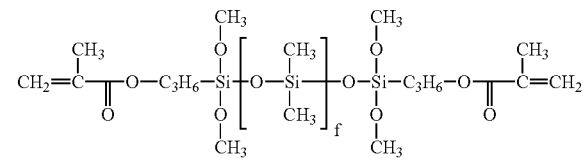

in which f=2 to 500,

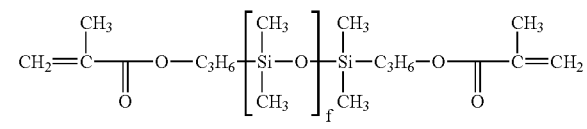

in which f=2 to 500, and

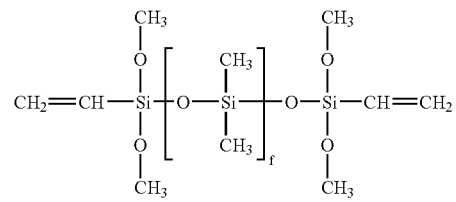

in which f=2-500,

E) optionally, one or more fluorine-containing component capable of free-radical polymerization and having a functionality of at least one, F) optionally, one or more olefinically mono- or polyunsaturated, macromonomer each possessing at least one oxygen, nitrogen, sulfur or phosphorus atom and having a number-average molecular weight of greater than or equal to 200 g/mol, the macromonomer not being a silicon-containing component D) or fluorine-containing component E), and G) optionally, the copolymerization taking place in the presence of at least one polymeric additive having number-average molecular weights of from 200 g/mol to $10^9$ g/mol.

2. The surfactant-free cosmetic, dermatological or pharmaceutical composition as claimed in claim 1, wherein the comonomer B) is selected from the group consisting of unsaturated carboxylic adds, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene, vinylphosphonic acid or the esters or salts thereof, vinylsulfonic acid or the esters or salts thereof, allylphosphonic acid or the esters or salts thereof methallyisulfonic acid or the esters or salts thereof, and mixtures thereof.

3. The surfactant-free cosmetic, dermatological or pharmaceutical composition as claimed in claim 1, wherein the comonomer C) are selected from the group consisting of diallyldimethylammonium chloride (DADMAC).
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride,
N-methyl-4-vinylpyridinium chloride,
dimethylaminoethyl methacrylate,
dimethylaminopropylmethacrylamide,
methacryloylethyl N-oxide,
methacryloylethylbetaine, and mixtures thereof.

4. The surfactant-free cosmetic, dermatological or pharmaceutical composition of claim 1, wherein the fluorine-containing component E) is a compound of the formula (II)

$$R^1—Y—C_rH_{2r}C_sF_{2s}CF_3 \quad (II)$$

where
R$^1$ is a polymerizable function from a vinylically unsaturated compounds;
Y is a chemical bridge, and
r, s are stoichiometric coefficients which independently of one another are numbers between 0 and 200.

5. The surfactant-free cosmetic, dermatological or pharmaceutical composition of claim 1, wherein the macromonomer F) is a compound of the formula (III)

$$R^1—Y—[(A)_v—(B)_w—(C)_x—(D)_z]—R^2 \quad (III)$$

where R$^1$ is a polymerizable function of a vinylically unsaturated compound;
Y is a bridging group;
A, B, C, and D independently of one another are discrete chemical repeating units, v, w, x, and z independently of one another amount to from 0 to 500, the sum of v, w, x, and z being on average $\geq 1$; and R$^2$ is a linear or branched aliphatic, olefinic, cycloaliphatic, arylaliphatic or aromatic (C$_1$-C$_{50}$) hydrocarbon radical, OH, —NH$_2$ or —N(CH$_3$)$_2$ or is [—Y—R$^1$].

6. The surfactant-free cosmetic, dermatological or pharmaceutical composition of claim 1 wherein the polymeric additives G) is selected from the group consisting of polyalkylene glycol; alkylpolyglycol; and mixtures thereof or a homopolymer or copolymer of a compound selected from the group consisting of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC), and [2-(methacryloyloxy)ethyl]trimethylammonium chloride (MAPTAC); and mixtures thereof.

7. The surfactant-free cosmetic, dermatological or pharmaceutical composition of claim 1, wherein the copolymerization takes place in the presence of at least one polymeric additive G).

8. The surfactant-free cosmetic, dermatological or pharmaceutical composition of claim 1, wherein the copolymers are crosslinked.

9. The surfactant-free cosmetic, dermatological or pharmaceutical composition of claim 1, wherein the copolymers are prepared by precipitation polymerization in tert-butanol.

10. The surfactant-free cosmetic, dermatological or pharmaceutical composition of claim 1, wherein the copolymers are water-soluble or water-swellable.

11. The surfactant-free cosmetic, dermatological or pharmaceutical composition of claim 1, which comprises, based on the finished composition, from 0.01 to 10% by weight of the copolymers.

12. The surfactant-free cosmetic, dermatological or pharmaceutical composition of claim 1, which has a pH of from 2 to 12.

13. The surfactant-free cosmetic, dermatological or pharmaceutical composition of claim 1, containing up to 70% by weight, of organic solvents, based on a finished composition.

14. The surfactant-free cosmetic, dermatological or pharmaceutical composition as claimed in claim 13, wherein the organic solvents are selected from the group consisting of monohydric alcohols, polyhydric alcohols, propylene glycol esters, sorbitol and Its derivatives, glycol ethers, propylene glycol ethers, and mixtures thereof.

15. The surfactant-free cosmetic, dermatological or pharmaceutical composition of claim 1, containing, based on a finished composition having an oil phase, up to 95% by weight, of the oil phase.

16. The surfactant-free cosmetic, dermatological or pharmaceutical composition as claimed in claim 15, wherein the oil phase comprises one or more oils selected from the group consisting of silicone oils, phenylsilicones, silicone resins, silicone gums, mineral oils, paraffin oils, vaseline oil, oils of animal origin, oils of plant origin, synthetic oils, linear and/or branched fatty alcohols, and linear and/or branched fatty acid esters, waxes, fluorinated oils, perfluorinated oils, and mixtures thereof.

17. The surfactant-free cosmetic, dermatological or pharmaceutical composition of claim 1, which is an emulsion or suspension.

18. The surfactant-free cosmetic, dermatological or pharmaceutical composition of claim 4 wherein, $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

19. The surfactant-free cosmetic, dermatological or pharmaceutical composition of claim 4, wherein the chemical bridge Y is selected from the group consisting of —O—, —C(O)—, —C(O)—O—, —S—, —O—CH$_2$—CH(O—)—CH$_2$OH, —O—CH$_2$—CH(OH)—CH$_2$—O—, —O—SO$_2$—O—, —O—S(O)—O—, —PH—, —P(CH$_3$)—, —PO$_3$—, —NH—, —N(CH$_3$)—, —O—(C$_1$-C$_{50}$)alkyl-O—, —O-phenyl-O—, —O-benzyl-O—, —O—(C$_5$-C$_8$)cycloalkyl-O—, —O—(C$_1$-C$_{50}$)alkenyl-O—, —O—(CH(CH$_3$)—(CH$_2$—O)$_n$—, —O—(CH$_2$—CH$_2$—O)$_n$—, —O—([CH—CH$_2$—O]$_n$—[CH$_2$—CH$_2$—O]$_m$)$_o$—, where n, m, and o independently of one another denote numbers from 0 to 200, and mixtures thereof.

20. The surfactant-free cosmetic, dermatological or pharmaceutical composition of claim 4 wherein, $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

21. The surfactant-free cosmetic, dermatological or pharmaceutical composition of claim 5, wherein Y is a bridging group selected from the group consisting of —O—, —S—, —C(O)—, —C(O)—O—, —O—CH$_2$—CH(O—)—CH$_2$OH, —O—CH$_2$—CH(OH)—CH$_2$O—, —O—SO$_2$—O—, —O—SO—O—, —PH—, —P(CH$_3$)—, —PO$_3$—, —NH—, —N(CH$_3$)—, and mixtures thereof.

22. The surfactant-free cosmetic, dermatological or pharmaceutical composition of claim 5 wherein the discrete repeating units of A, B, C, and D are originating from a unit selected from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

23. The surfactant-free cosmetic, dermatological or pharmaceutical composition of claim 5 wherein the discrete repeating units of A, B, C, and D are originating from a unit of ethylene oxide or propylene oxide.

24. The surfactant-free cosmetic, dermatological or pharmaceutical composition of claim 5, wherein v, w, x, and z independently of one another amount to from 1 to 30.

25. The surfactant-free cosmetic, dermatological or pharmaceutical composition of claim 5 wherein, $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

26. The surfactant-free cosmetic, dermatological or pharmaceutical of claim 14, which contains from 2 to 50% by weight of the oil phase.

27. A surfactant-free cosmetic, dermatological or pharmaceutical composition which is free of surfactant and comprises at least one copolymer obtained by free-radical copolymerization of acryloyldimethyltaurine and/or acryloyldimethyltaurates, and
one or more silicon-containing component a) capable of free-radical polymerization and having a functionality of at least one, where at least one silicon-containing component a) is a compound selected from the formulae

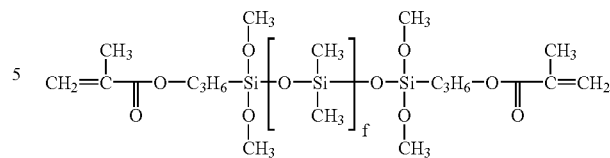

in which f=2 to 500,

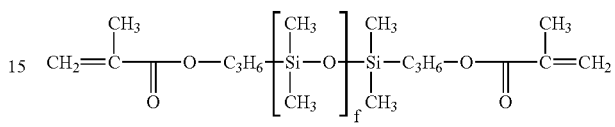

in which f=2 to 500, and

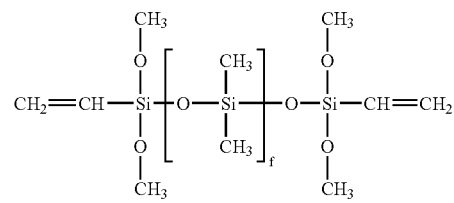

in which f=2-500.

28. The acidic cosmetic, dermatological or pharmaceutical composition of claim 27, wherein said copolymerization further comprises a component selected from the group consisting of
b) one or more fluorine-containing component capable of free-radical polymerization and having a functionality of at least one,
c) one or more olefinically mono- or polyunsaturated, macromonomer each possessing at least one oxygen, nitrogen, sulfur or phosphorus atom and having a number-average molecular weight of greater than or equal to 200 g/mol, the macromonomer not being the silicon-containing component a) or the fluorine-containing component b),
d) at least one polymeric additive having number-average molecular weights of from 200 g/mol to $10^9$ g/mol,
e) one or more further olefinically unsaturated, noncationic comonomer which have at least one oxygen, nitrogen, sulfur or phosphorus atom and possess a molecular weight of less than 500 g/mol,
f) one or more olefinically unsaturated, cationic comonomer which has at least one oxygen, nitrogen, sulfur or phosphorus atom and possess a molecular weight of less than 500 g/mol, and a mixture thereof.

29. The surfactant-free cosmetic, dermatological or pharmaceutical composition of claim 28, wherein said macromonomer c) is crosslinking.

30. The surfactant-free cosmetic, dermatological or pharmaceutical composition of claim 28, wherein said olefinically unsaturated, noncationic comonomer e) is crosslinking.

* * * * *